United States Patent
Heitmeier

(10) Patent No.: US 6,544,228 B1
(45) Date of Patent: Apr. 8, 2003

(54) INFUSION DEVICE COMPRISING A PLURALITY OF INFUSION PUMPS

(75) Inventor: Rolf Heitmeier, Baunatal (DE)

(73) Assignee: B. Braun Melsungen AG, Melsungen (DE)

( * ) Notice: Subject to any disclaimer, the term of this patent is extended or adjusted under 35 U.S.C. 154(b) by 116 days.

(21) Appl. No.: 09/722,296

(22) Filed: Nov. 28, 2000

(30) Foreign Application Priority Data

Dec. 24, 1999 (DE) .......................................... 299 22 736

(51) Int. Cl.[7] .......................... A61M 37/00; F04B 41/06
(52) U.S. Cl. ............................ 604/131; 340/3.5; 417/2; 604/65; 700/2; 700/283
(58) Field of Search ................................ 700/282, 283; 417/2, 17; 236/51; 604/30, 65, 131; 340/3, 5

(56) References Cited

U.S. PATENT DOCUMENTS

| | | | |
|---|---|---|---|
| 4,756,706 A | | 7/1988 | Kerns et al. ................... 604/69 |
| 5,927,398 A | * | 7/1999 | Maciulewicz ............. 236/51 X |
| 5,959,539 A | * | 9/1999 | Adolph et al. ................ 340/3.5 |
| 6,123,686 A | * | 9/2000 | Olsen et al. ................. 604/151 |
| 6,358,237 B1 | * | 3/2002 | Paukovits et al. .......... 604/516 |

\* cited by examiner

Primary Examiner—William Wayner
(74) Attorney, Agent, or Firm—Diller, Ramik & Wight

(57) ABSTRACT

The infusion device comprises a central controller (10) and a plurality of infusion apparatus (12) each connected via a data channel (15) with the controller (10). Each infusion apparatus (12) is provided with a unique identification number. When an infusion apparatus (12) is connected to the controller (10) the identification number is requested and the controller (10) checks whether this identification number has already been allocated. If this is not the case, the controller (10) sends the inverted identification number back to the infusion apparatus (12). The infusion apparatus (12) accepts commands from the controller (10) only if the returned signal corresponds to the identification number.

7 Claims, 2 Drawing Sheets

INFUSION DEVICE COMPRISING A PLURALITY OF INFUSION PUMPS

BACKGROUND OF THE INVENTION

The present invention relates to an infusion device comprising a pump system having a plurality of infusion pumps and a central controller communicating via data channels with the individual infusion pumps.

The more and more complex medication of intensive-care patients requires central preparation of the medication data. The technical solutions previously referred to as documentation systems do not allow, for safety-relevant considerations, remote control of the infusion pumps. An essential reason for this restriction is that programmable systems of single-channel structure do not prevent the occurrence of a first error. For this reason dual-channel structures were created. This solved the problem of undetected arithmetical errors and undetected changes in the memory but did not help to attain the necessary overall safety required for connecting two systems operating perfectly from the safety point of view. This becomes evident when an infusion system, which may comprise nine pumps or other medical apparatus, is to be combined to form an overall system with the safety aspects being taken into consideration. The prerequirements for such a solution are:

- unambiguous identification of each individual infusion apparatus,
- prevention of falsification of data owing to physical one-channel transmission,
- prevention of incorrect allocation (addressing) of infusion apparatus,
- detection of removal of an infusion apparatus from the infusion system,
- parallel automatic/manual operation,
- action-dependent infusion, i.e. bolus administration for the duration of a key depression.

It is an object of the present invention to provide an infusion device comprising a central controller and a plurality of infusion apparatus, which meets the safety requirements to a large extent.

SUMMARY OF THE INVENTION

According to the invention each infusion apparatus is provided with a unique identification number. After connection of a pump the infusion device carries out an identification process with the unique identification number of the infusion apparatus being the central element of this identification process. The controller is requested to ask, prior to the remote control, for the identification number of the newly detected infusion apparatus. Then the infusion apparatus transmits the identification number to the controller which checks whether this identification number has already been allocated. If this is the case, the identification number is sent back to the infusion apparatus either in unchanged or in modified form. Only when the signal returned has been detected as correct the infusion apparatus will accept remote control commands from the controller. By checking the identification number the controller ensures that the identification number has been allocated only once in the infusion system concerned. This prevents the use of identification numbers which have by mistake been allocated more than once. On the other hand, the infusion apparatus recognizes on the basis of the returned signal that the controller has completed a check of the identification number with positive result and accepts only then the remote control commands from the controller. The present invention ensures that a data-addressable infusion apparatus exists only once in the system and can be clearly identified. It is prevented that two infusion apparatus bear the same identification number, which would result in parallel addressing of the two infusion apparatus by the control computer and thus in unintended overdosing.

Preferably the signal sent back by the controller and corresponding to the identification number is the inverted identification number. This means that the 0-bits are converted into 1-bits and the 1-bits into 0-bits. These simple logic means allow a comparison between the identification number and the modified identification number. Of course, more complex modifications of the identification number are possible.

The problem regarding falsification of data due to the physical one-channel transmission is solved according to a preferred aspect of the invention in that the controller and the control unit of the infusion apparatus are of dual-channel configuration and that one channel provides the data to be transmitted, while the other channel generates a password corresponding to said data. This means that the data safeguarding processes, where a password depending on the contents of the code word is generated for each code word, are transferred to the dual-channel technique with one channel transmitting the codeword (data) and the other channel generating the password. Code word and password are transmitted via the unique data channel. The dual-channel structure of controller and infusion apparatus is used for data safeguarding purposes. While the first channel makes available the data to be transmitted, the second channel generates independently of the first one the respective password. The password is for example a CRC polynominal. It is ensured that a password is not by accident added or generated by a data-providing channel.

The data generated by the controller must reach the respective infusion apparatus without mistaken identification. This is realized by using the identification number. The data safeguarded by a password are further labelled by adding an identification number. The infusion apparatus checks the labelled data for correspondence with its own identification number. Only in the case of correspondence the data wil be accepted.

Removal of the infusion apparatus from the system or unintended interruption of the connection between infusion apparatus and controller may result in overdosing when for example the rate to be supplied by the respective infusion apparatus is continuously changed by a control algorithm in the controller. The infusion apparatus expects a valid sequence of communication with the controller within a given fault tolerance time. When no communication sequence occurs, the medication is stopped and switched to a regime which cannot harm the patient.

The controller is preferably configured such that it is adapted to perform two modes of operation with interventions in the operation of the infusion apparatus being accepted and adjustments to the controller being ignored in a "remote control" mode of operation, and interventions in the operation of the infusion apparatus being ignored and adjustments to the controller being accepted in a "remote regulation" mode of operation. This solves the problem of parallel operation which occurs since controller and infusion apparatus can be separately operated. Thus it is possible that the controller sets the infusion rate to the value XXX due to a time-variant rate control, while the user adjusts the value YYY on the infusion apparatus. To solve this problem the invention provides both m odes of operation.

According to a further aspect of the present invention the infusion device allows action-dependent infusion. This may be a situation in which a defined flow rate is supplied to the infusion apparatus as long as a key is pressed or the user panel of the controller is actuated, or the infusion apparat us has to feed a rate XXX for the duration of a key depression. According to the present invention the key depression is transferred in small time segments. The controller requires at regular intervals repetition or maintaining of the key depression. If the key depression is not repeated or maintained, this state is interpreted as the key no longer being pressed and the infusion is stopped.

DESCRIPTION OF THE PREFERRED EMBODIMENT

Figure 1:
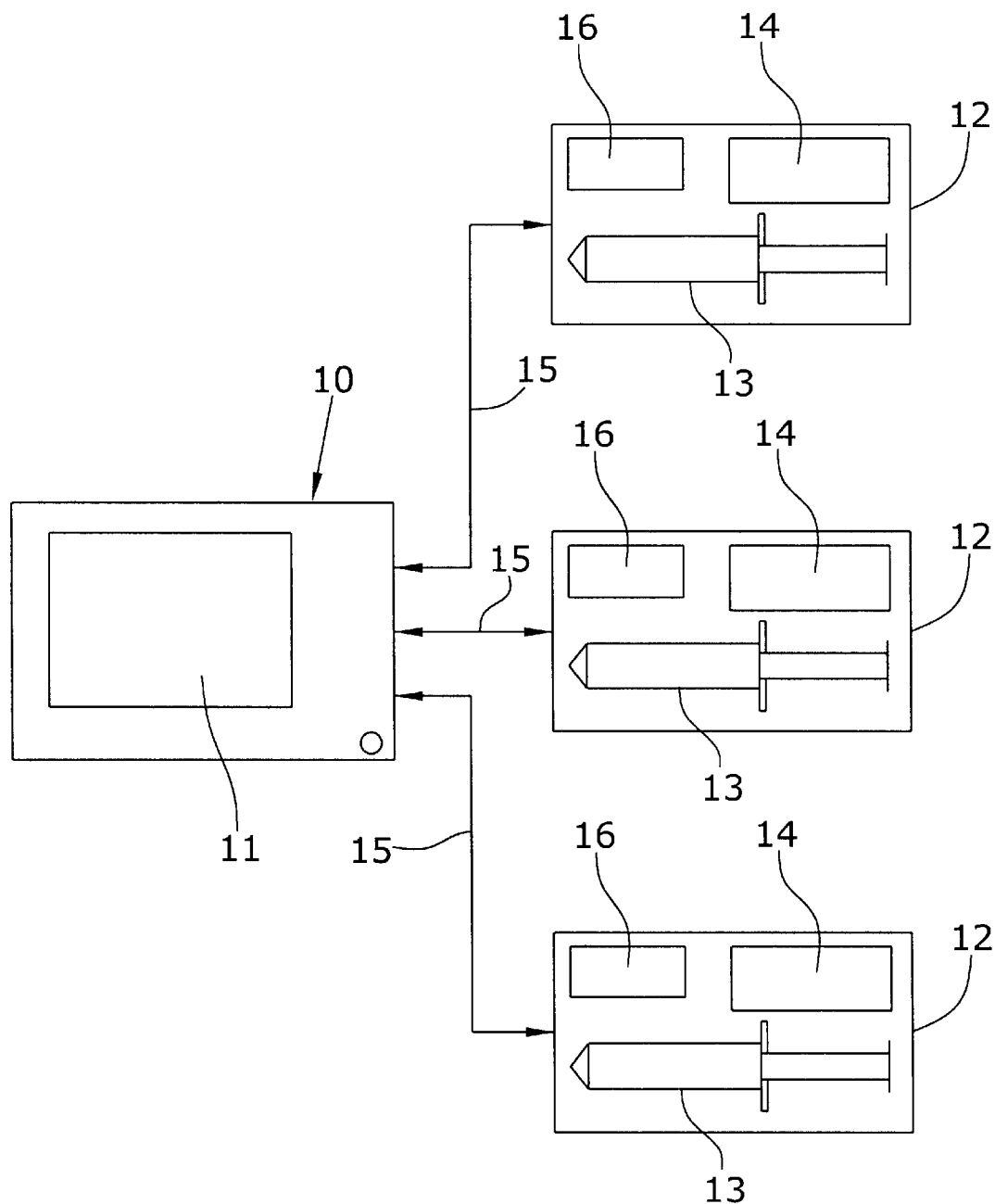
FIG. 1 and FIG. 2. show a block diagram and a flow chart, respectively, of an infusion device constructed in accordance with the invention.
Figure 2:
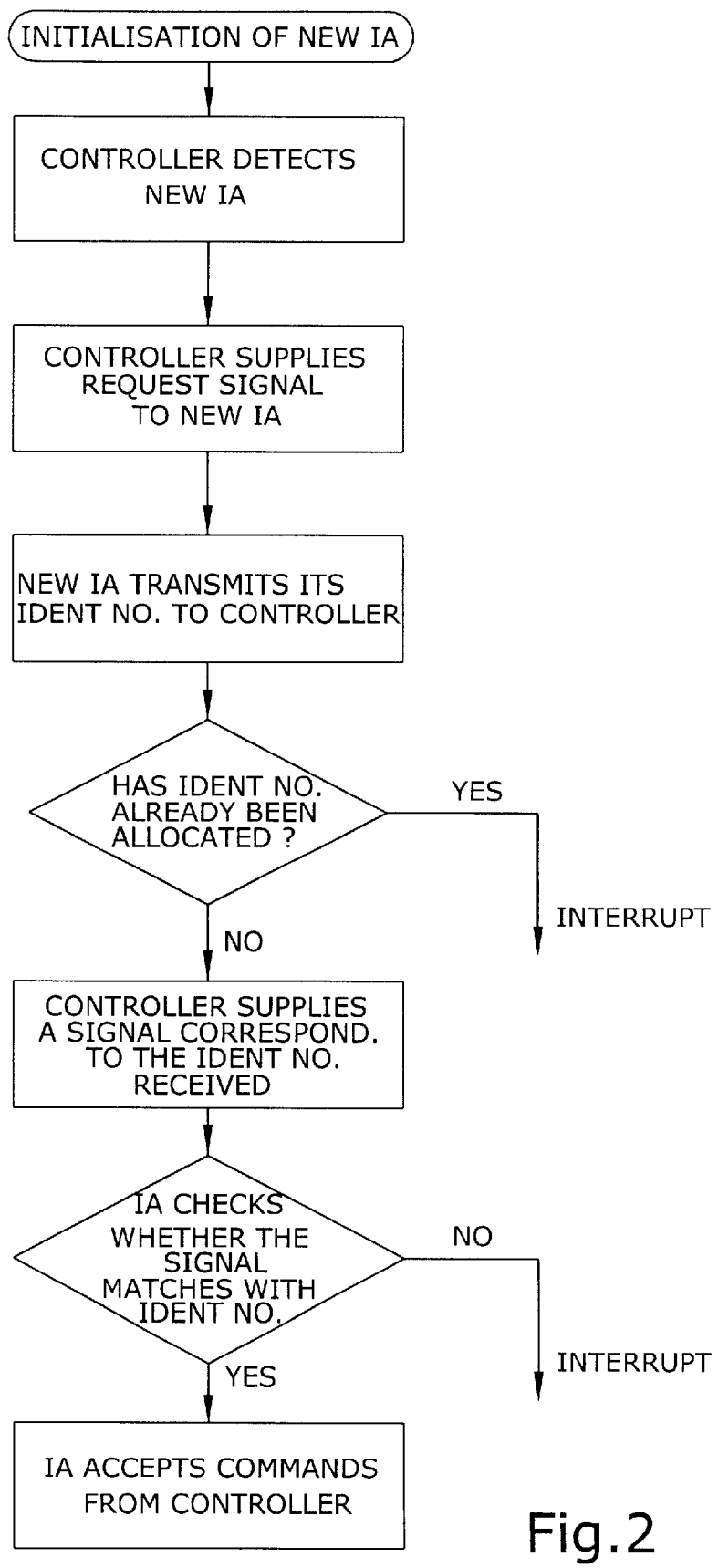

The infusion device comprises a central controller 10 having a control computer and a display screen 11 as well as a data entry keyboard (not shown). The display screen 11 can be configured as touch screen and used as data entry keyboard.

The infusion device further comprises a system of a plurality of infusion apparatus 12. Said infusion apparatus 12 are preferably infusion pumps, in particular syringe pumps. In the case of a syringe pump the contents of a syringe 13 comprising syringe barrel and piston is pressed out and transferred via a catheter to the patient's body. Pressing the contents out of the syringe 13 is effected by controlled advancing of the syringe piston via the infusion pump actuator.

The infusion device 12 further comprises a control unit 14 which is a computer communicating with the controller 10. Data communication takes place via data channels 15. The data channel 15 is provided as an electrical line, in particular an interference-proof twisted line or a coaxial cable. The data channel 15 may also be configured as a wireless radio channel. All infusion devices 12 connected to the controller 10 are allocated to the same patient, i.e. their fluid lines are connected via a line system with the patient's body.

Each infusion device 12 further comprises a data entry and display device 16. When an infusion apparatus 12 has been connected to the controller 10, the dual-channel control computer in the controller 10 asks the infusion apparatus 12 for the identification number. The identification number is entered into the infusion apparatus 12 in the manufacturer's works. It is a unique identification number allocated to this specific infusion apparatus 12. Then the infusion apparatus 12 transmits the identification number to the control computer which checks whether this identification number has already been allocated. If this is not the case, the identification number is inverted and sent back to the infusion apparatus 12. Only after checking the correctness of the inverted identification number the infusion apparatus 12 will accept remote control commands from the controller 10.

The control commands and other data are transmitted together with a fault detection code. For this purpose known data safeguarding processes are applied, for example use of a CRC polynominal as password. In this connection the dual-channel systems in the control computer and the infusion apparatus 12 are utilized in that one channel makes available the data to be transmitted, while the other channel generates the associated CRC safeguarding sum independent of the first channel.

The respective identification number of the addressed controller 10 is transmitted together with the commands and data.

Each infusion apparatus 12 expects a valid sequence of communication with the controller 10 within a given fault tolerance time. When no communication sequence occurs due to an interrupted data communication path, the infusion apparatus is taken out of operation and switched to a regime which cannot harm the patient.

The system provides two modes of operation, namely the "remote-control" mode of operation where interventions in the operation of the infusion apparatus 12 are accepted and adjustments to the controller 10 are ignored, and the "remote regulation" mode of operation where interventions in the operation of the infusion apparatus 12 are ignored and adjustments to the controller are accepted.

In the controller 10 a key is provided as independent key or as touch screen key upon the actuation of which the infusion apparatus 12 has to supply a predetermined adjustable infusion rate for the duration of the key depression. The key depression is detected in predetermined short time segments. If within one of these successive intervals no key depression is detected, this is interpreted as the key no longer being pressed and the infusion is stopped.

Although a preferred embodiment of the invention has been specifically illustrated and described herein, it is to be understood that minor variations may be made in the device without departing from the spirit and scope of the invention, as defined in the appended claims.

What is claimed is:

1. Infusion device comprising a central controller (10) and a plurality of infusion apparatus (12) communicating via data channels (15) with the controller (10), wherein each infusion apparatus (12) is provided with a unique identification number, the controller (10) detects via the data channel (15) whether a new infusion apparatus (12) has been connected and supplies a request signal to said infusion apparatus (12), the infusion apparatus (12) transmits its identification number to the controller (10) in response to the request signal with the controller (10) checking whether this identification has already been allocated, the controller (10) supplies a signal corresponding to the identification number received to the infusion apparatus (12), and the infusion apparatus (12) determines whether the signal supplied by the controller (10) matches the identification number and accepts commands from the controller (10) only in the affirmative case.

2. Infusion device according to claim 1, wherein the identification number corresponding to the signal is a modified identification number.

3. Infusion device according to claim 1, wherein the controller (10) and the control unit (14) of the infusion apparatus (12) are of dual-channel configuration and one channel makes available the data to be transmitted, while the other channel generates a password corresponding to the data.

4. Infusion device according to claim 3, wherein the data safeguarded by the password are labelled by the identification number of the infusion apparatus (12) destined as receiver, the infusion apparatus (12) accepting the data only when they correspond to its identification number.

5. Infusion device according to claim 1, wherein the infusion apparatus (12) expects a valid sequence of communication with the controller (10) within a predetermined fault tolerance time and stops medication if said sequence of communication does not take place.

6. Infusion device according to claim 1, wherein the controller (10) is adapted to perform two modes of operation with interventions in the operation of the infusion apparatus (12) being accepted and adjustments to the controller (10) being ignored in a "remote control" mode of operation, and interventions in the operation of the infusion apparatus (12) being ignored and adjustments to the controller (10) being accepted in a "remote regulation" mode of operation.

7. Infusion device according to claim 1, wherein a key depression is detected in short intervals and the absence of the key depression within a predetermined interval is interpreted as a key no longer being pressed which results in interruption of the infusion process.

* * * * *